US00PP36322P2

(12) United States Plant Patent
Evison

(10) Patent No.: US PP36,322 P2
(45) Date of Patent: Dec. 17, 2024

(54) ***CLEMATIS* PLANT NAMED 'EviGsy153'**

(50) Latin Name: ***Clematis palens* X *viticella***
Varietal Denomination: EviGsy153

(71) Applicant: Raymond J. Evison Ltd., Vale (GB)

(72) Inventor: Raymond J. Evison, Vale (GB)

(73) Assignee: RAYMOND J. EVISON LTD., Vale (GB)

( * ) Notice: Subject to any disclaimer, the term of this patent is extended or adjusted under 35 U.S.C. 154(b) by 0 days.

(21) Appl. No.: 18/509,228

(22) Filed: Nov. 14, 2023

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
CPC ..... A01H 5/02; A01H 5/00; A01H 6/72
See application file for complete search history.

(56) References Cited

PUBLICATIONS

Linkedin. The Guernsey Clematis Nursery Ltd's Post, retrieved on Mar. 12, 2024 at https://www.linkedin.com/posts/the-guernsey-clematis-nursery-ltd_just-got-home-after-a-great-couple-of-days-activity-7077386125522202624-xQtk, 10 pp. (Year: 2024).*
The HTA National Plant Show 2023, retrieved on Mar. 12, 2024 at https://hta.org.uk/national-plant-show-2023, 3 pp. (Year: 2024).*

* cited by examiner

*Primary Examiner* — June Hwu
(74) *Attorney, Agent, or Firm* — Penny J. Aguirre

(57) ABSTRACT

A new cultivar of *Clematis* plant named 'EviGsy153' that is characterized by its flowers that are large in size (up to 24 cm in diameter), its flowers that are white in color with non-prominent brownish red anthers, its repeat flowering; blooming from May through July and re-blooming in late August and September, its thick tepals resulting in long-lasting flowers, its compact plant habit (90 cm to 1.2 m in height), its floriferous blooming habit, its good suitability for use in gardens and in containers and its flowers that initially open slowly and holding its tepals together in a "Champagne Flute" like manner before fully opening; this feature in addition to its thick tepals results in an exceptionally long flower life.

2 Drawing Sheets

Botanical classification: *Clematis patens* X *viticella*.
Variety denomination: 'EviGsy153'.

BACKGROUND OF THE INVENTION

The present invention relates to a new and distinct cultivar of *Clematis* of hybrid origin and will be referred to hereafter by its cultivar name 'EviGsy153'. 'EviGsy153' is grown as an herbaceous climbing plant for use in the landscape or as a flowering potted plant for the terrace.

'EviGsy153' derived from an ongoing breeding program by the Inventor at his nursery in Guernsey, The Channel Islands. The goal of the breeding program is to select new cultivars of *Clematis* with a compact plant habits with an abundance of flowers that are large in size with unique flower colors. 'EviGsy153' was selected as a single unique plant in May of 2019 and arose from a controlled cross made in June of 2014 between unnamed and unpatented proprietary seedlings of *Clematis patens* X *viticella* from the Inventor's breeding program as both the female and male parents.

Asexual propagation of the new cultivar was first accomplished by stem cuttings under the direction of the Inventor in Guernsey, The Channel Islands in May of 2019. Asexual propagation by internodal stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'EviGsy153' as a unique cultivar of *Clematis*.

1. 'EviGsy153' exhibits flowers that are large in size (typically 18 cm but can reach up to 24 cm in diameter).
2. 'EviGsy153' exhibits flowers that are white in color with non-prominent brownish red anthers.
3. 'EviGsy153' exhibits repeat flowering; blooming from May through July and re-blooming in late August and September.
4. 'EviGsy153' exhibits flowers with thick tepals resulting in long-lasting flowers.
5. 'EviGsy153' exhibits a compact plant habit (90 cm to 1.2 m in height).
6. 'EviGsy153' exhibits a floriferous blooming habit.
7. 'EviGsy153' exhibits good suitability for use in gardens and in containers.
8. 'EviGsy153' exhibits flowers that initially open slowly and holding its tepals together in a "Champagne Flute" like manner before fully opening; this feature in addition to its thick tepals results in an exceptionally long flower life.

The female parent of 'EviGsy153' differs from 'EviGsy153' in having flowers with tepals that are white with a red-purple central bar on the tepals and more prominent stamens. The male parent of 'EviGsy153' differs from 'EviGsy153' in having flowers with blue tepals and yellow anthers. 'EviGsy153' can be most closely compared to the *Clematis* cultivars 'Evipo097' (U.S. Plant Patent Abandoned, Publication No, U.S. 2022/0071074 P1), marketed as Boulevard® Kitty™, 'Evipo021' (U.S. Plant Pat. No. 16,191), and 'Evipo052' (U.S. Plant Pat. No. 28,600). 'Evipo097' is similar to 'EviGsy153' in flower color. 'Evipo097' differs from 'EviGsy153' in having smaller flowers, a more compact plant habit, and tepal margins that are more undulate and more prone to recurve at a younger age. 'Evipo021' is similar to 'EviGsy153' in flower size. 'Evipo021' differs from 'EviGsy153' in having flowers with white tepals that have a red-purple central bar. 'Evipo052' is similar to 'EviGsy153' in flower color. 'Evipo052' differs from 'Evipo052' in having flowers with tepals with a more prominent center (domed) and a more compact plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Raymond Evison *Clematis*, Thorncroft *Clematis*, The Guernsey *Clematis* Nursery, Floral Daily, AIPH, Linkedin, BPnieuws, Gardenforum, Crocus, Bay View Garden Centre (Instagram), Garden Centre Plants, Waitrose Garden, Garden Forum, and Plantago.

BRIEF DESCRIPTION OF THE DRAWINGS

The accompanying color photographs illustrate the overall appearance and distinct characteristics of the new *Clematis*. The photographs were taken of a 2.5-year-old plant of 'EviGsy153' as grown in a 17-cm container in a conventional greenhouse in in Guernsey, The Channel Islands.

The photograph in FIG. 1 shows the plant habit of 'EviGsy153' in bloom.

Figure 1:
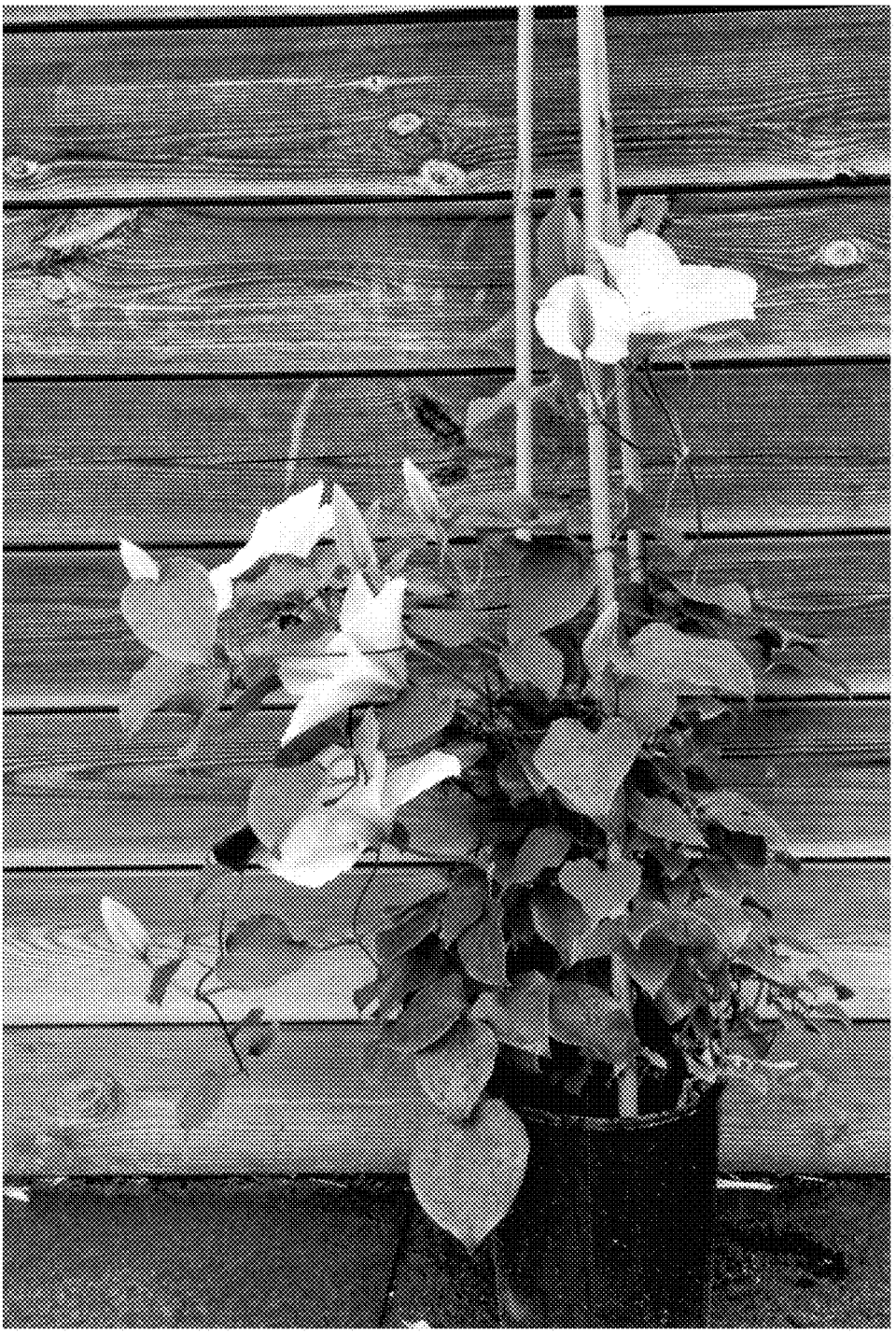
Figure 2:
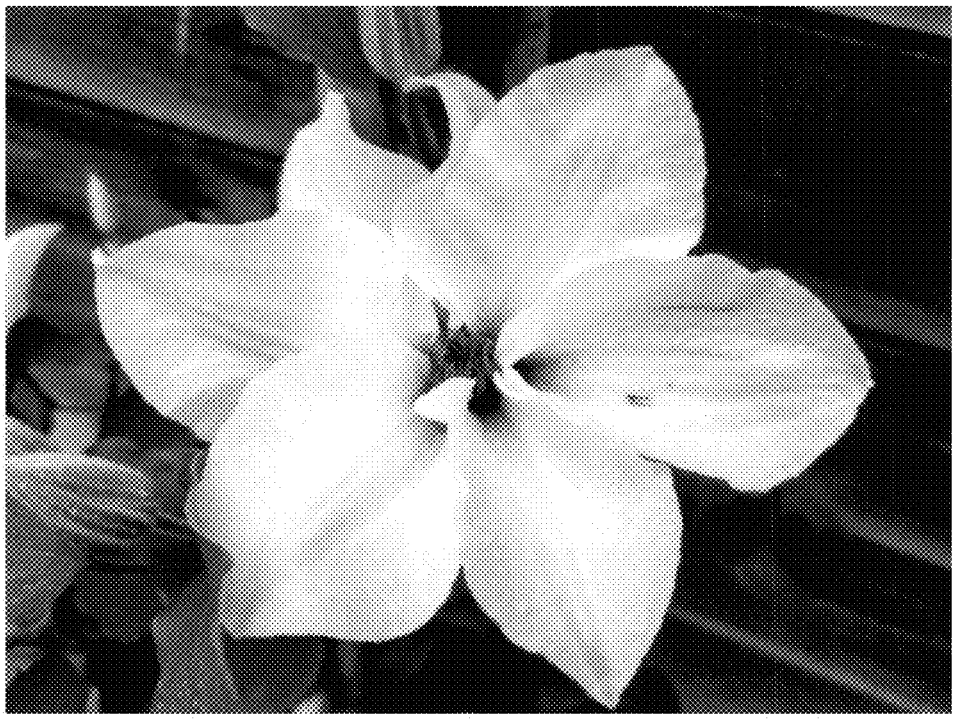

The photograph in FIG. 2 provides a close-up view of a maturing flower of 'EviGsy153'.

Figure 3:
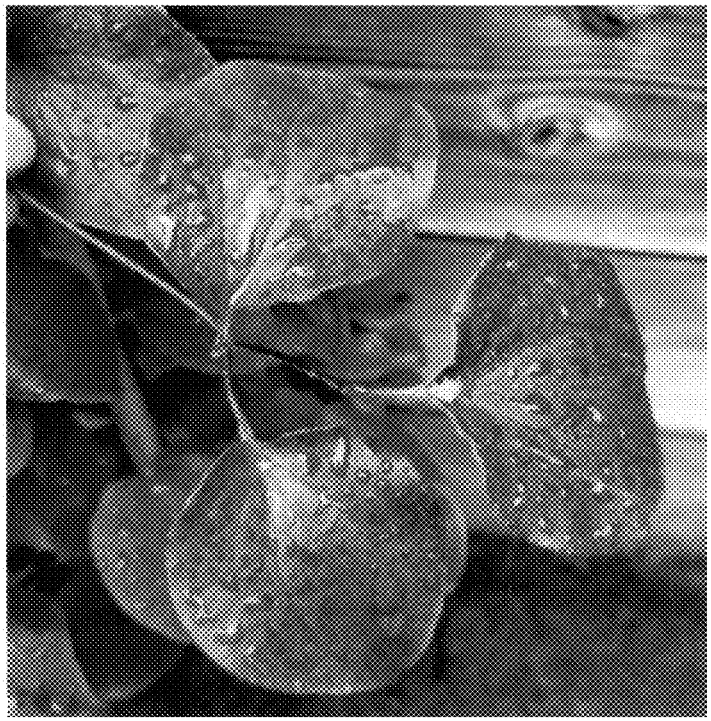

The photograph in FIG. 3 provides a close-up view of a leaf of 'EviGsy153'.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of 2.5-year-old plants of 'EviGsy153' as grown in 17-cm containers in Guernsey, The Channel Islands. Plants were cut back to about 15 cm in late winter to early spring. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from May to July and reblooms in late August and September in Guernsey, The Channel Islands.

*Plant type*.—Herbaceous woody vine, early blooming large flowering *Clematis* that blooms on both old and new wood.

*Plant habit*.—Climber, blooms on new wood, compact.

*Height and spread*.—Average of 59 cm in height, 40 cm in width as a 2.5-year-old plant in a container, seasons growth in the landscape attains 90 to 120 cm in height and 50 to 60 cm in spread.

*Hardiness*.—At least in U.S.D.A. Zones 4 to 9.

*Diseases*.—No susceptibility or resistance to pests and diseases has been observed.

*Root description*.—Fleshy.

*Propagation*.—Softwood cuttings from vegetative shoots.

*Time required for root initiation*.—Roots initiate in 3 to 4 weeks, another 4 to 6 weeks to produce a fully rooted cutting ready for potting, root development from plug to P7 is 3 to 6 months, 30 weeks to mature in a P12 container.

*Growth rate*.—Moderate.

Stem description:

*Shape*.—Round.

*Stem color*.—Young; 144A to 144B, mature and older; N199C to N199D.

*Stem size*.—Length from base to flowering portion of the stem; 49 cm in length, diameter; 3 mm.

*Stem surface*.—Very sparsely pubescent.

*Stem strength*.—Strong.

*Internode length*.—Average of 10 cm.

*Branching*.—Basal branching.

Foliage description:

*Leaf arrangement*.—Opposite, ternate.

*Leaf division*.—Compound.

*Leaf attachment*.—Petiolate.

*Leaf quantity*.—10 per stems, 3 leaflets per whole leaf.

*Leaf size*.—Average of 6.9 cm in length and 5.6 cm in width.

*Leaflet shape*.—Broadly ovate.

*Leaflet base*.—Rounded.

*Leaflet apex*.—Acute.

*Leaflet fragrance*.—None.

*Leaflet venation*.—Palmate, color; young upper surface 144C, young lower surface 146A to 146B, mature upper surface 137A, mature lower surface mid-rib 144A and 137B to 137C.

*Leaflet margins*.—Entire.

*Leaflet attachment*.—Petiolule.

*Leaflet surface*.—Upper surface glabrous, glossy, lower surface matte.

*Leaflet size*.—Average of 4 cm in length and 3 cm in width.

*Leaflet color*.—Young upper surface; 144A, young lower surface 146A to 146B, mature upper surface 137B, mature lower surface 137B to 137C.

*Petioles*.—Up to 8 cm in length, 2 mm in width, 144A, flushed with 183B, sparsely pubescent surface.

*Petiolules*.—Up to 4.6 cm in length, 1 to 2 mm in diameter, 144A, flushed with 183B, sparsely pubescent surface.

Inflorescence description:

*Inflorescence type*.—Solitary; from one to 4 at upper axils.

*Inflorescence arrangement*.—Terminal and axillary on new growth.

*Pedicel*.—5.9 cm in length, 4 mm in diameter, 144B in color, glabrous surface, moderate strength.

*Bud description*.—Ovoid in shape, 5 cm in length, 1.9 cm in width, 145B to 145D in color, pubescent surface.

*Flower fragrance*.—No.

*Lastingness of flowers*.—Long lasting individual flowers last about 14 days, self-cleaning.

*Flower quantity*.—4 open flowers, 10 buds.

*Flower type*.—Single, rotate, spreading, star-shaped.

*Flower aspect*.—Upward, rotate, held open in a tubular shape when opening and becomes flat as they mature.

*Flower size*.—Average of 14.3 cm in diameter (up to 24 cm in diameter) and 5 cm in depth.

*Tepal number*.—7.

*Tepal shape*.—Broadly elliptic.

*Tepal apex*.—Acuminate.

*Tepal base*.—Acute.

*Tepal margins*.—Entire with very light undulations.

*Tepal surface*.—Both surfaces glabrous, satiny and matte.

*Tepal color*.—When opening and fully open upper surface; N155D, base and tip 145A to 145B, mid-rib 145C, older flowers upper surface N155D, base and tip 145B, mid- rib 145C to 145D, when opening and fully open lower surface; N155B, base and tip 145A, mid-rib 145B to 145C, older flowers; 155B, base 145A, mid-rib and tip 145C to 145D.

*Tepal size*.—Average of 6.8 cm in length and 3.6 cm in width.

*Tepal arrangement*.—Overlapping.

*Receptacle*.—7 mm in depth, 9 mm in width, pubescent surface, round in shape, 144B in color.

Reproductive organs:

*Gynoecium*.—Pistils; between 70 and 80, style; 1.4 cm in length, 1 mm in diameter, color 157D, 145C at the base, stigma; slightly superior relative to the length of the filaments and height of the anthers, very small and hard to see, ovary; 145B in color.

*Androecium*.—Stamens; 120, filaments; 9 mm in length, glabrous surface, 144C to 144D in color, anthers; 8 mm in length, linear in shape, 174A in color, glabrous, pollen was not observed.

*Seed*.—Seed head; an average of 2.1 cm in length, 2.6 cm in width, shiny hairs, style; plumose at base, color; 144C and 165A to 165B, seed development was not observed.

It is claimed:

1. A new and distinct cultivar of *Clematis* plant named 'EviGsy153' as herein illustrated and described.

* * * * *